United States Patent [19]

Ohshiro et al.

[11] Patent Number: 4,905,690
[45] Date of Patent: Mar. 6, 1990

[54] SEMICONDUCTOR LASER TREATMENT DEVICE

[75] Inventors: Toshio Ohshiro, Tokyo; Tokuharu Hayashi, Kanagawa, both of Japan

[73] Assignee: Medical Laser Research Co., Ltd., Japan

[21] Appl. No.: 325,038

[22] Filed: Mar. 16, 1989

Related U.S. Application Data

[63] Continuation of Ser. No. 117,173, Oct. 5, 1987, abandoned.

[30] Foreign Application Priority Data

Jun. 30, 1986 [JP] Japan .................................. 61-151551
Sep. 10, 1986 [JP] Japan .................................. 61-211665
Dec. 26, 1986 [WO] PCT Int'l Appl. ... PCT/JP86/00666

[51] Int. Cl.$^4$ ............................................. A61B 17/36
[52] U.S. Cl. ..................................... 128/395; 128/397
[58] Field of Search ................. 128/6, 303.1, 395–398, 128/664

[56] References Cited

U.S. PATENT DOCUMENTS

| | | | |
|---|---|---|---|
| 4,232,678 | 11/1980 | Skovajsa | 128/395 |
| 4,311,142 | 1/1982 | Machida | 128/395 |
| 4,423,726 | 1/1984 | Imagawa et al. | 128/395 |
| 4,469,098 | 9/1984 | Davis | 128/395 |
| 4,494,550 | 1/1985 | Blazek et al. | 128/664 |
| 4,621,284 | 11/1986 | Nishicka et al. | 128/6 |

OTHER PUBLICATIONS

"Semiconductor Laser Medical Device", Saeki, English Translation of Jap. Pat. No. 61-137548, Jun. 29, 1986.
"Disconnectable Coupling ... Device", Wondracek et al., English Translation of Jap. Pat. No. 61-141351, Jun. 28, 1986.
"Laser Irradiation Device", Kinoshi, English Translation of Jap. Pat. No. 60-33967, Oct. 9, 1985.
"Semiconductor Laser Medical Device", Saeki et al., English Translation of Jap. Pat. No. 61-234877, Oct. 20, 1986.

Primary Examiner—Max Hindenburg
Attorney, Agent, or Firm—Klauber & Jackson

[57] ABSTRACT

This semiconductor laser treatment unit is constructed of a laser radiation device 1 and a control box 67 which houses a control mechanism for controlling this laser radiation device 1. The laser radiation device has at its tip a cap 3 which has a pair of touch sensors 69 in the vicinity of a laser emission aperture 68, multiple semiconductor lasers 10, and a series of lenses which make the laser beams emitted from the semiconductor lasers parallel and also focus them to a single point to form a laser beam for use in medical treatment. Further the unit is provided with a means of adjusting the degree of convergence required to create a medical treatment laser beam from the laser beams emitted from multiple semiconductor lasers, a means of precisely and easily determining the status of laser beam emission, thus making the device easier to use and enhancing its safety during use, and a means of eliminating any unpleasant sensation caused to the patient by the touch sensors 69.

7 Claims, 5 Drawing Sheets

SEMICONDUCTOR LASER TREATMENT DEVICE

This is a continuation of application Ser. No. 117,173, filed 10/5/87, now abandoned.

TECHNICAL FIELD

The semiconductor laser treatment unit of this invention consists of a laser radiation device and a control box which houses a control mechanism used to control the laser radiation device via a cable. The said laser radiation device is provided at its tip with a cap which has a pair of touch sensors in the vicinity of the emission aperture. It also is provided internally with multiple semiconductor lasers, and lenses for focusing to a single point individual laser beams radiated in parallel from these multiple semiconductor lasers, thus forming an optical laser beam used in medical treatment.

BACKGROUND TO THE INVENTION

Previously known semiconductor laser treatment devices have been described in, for example, Japanese Patent Publication (Toku-kai) Sho 58-86178, 58-89278, and 59-105445. However, this prior art had the following defects which needed improvement.

The first problem involved the means of regulating the degree of convergence of the laser beams emitted from the multiple semiconductor lasers. In other words, the luminous output of the semiconductor lasers used today is restricted. To obtain the intensity of beam output required for use in medical treatment, multiple semiconductor lasers have to be combined, and the laser beams from them focused at a particular point. To achieve this, laser beams are emitted from multiple semiconductor lasers, and the output beams are aligned in parallel by the corresponding first lenses, and are made to fall on the second lens at right angles and at a specified place on its circumference. However, because the quality of the laser beam varies, and because the laser beam emission position, ie the part emitting the radiated beam, may be positioned slightly higher or lower, or further to the front or rear, and the angle of laser beam emission varies, it is difficult to obtain the desired angle of incidence of the laser beams without adjusting the relative positions of the semiconductor laser, first lens and second lens. Various adjustments are then required, such as the positioning of the semiconductor lasers and the corresponding first lenses at the specified circumference in relation to the second lens, within a precision of several tens to several microns, then aligning the emission points of the semiconductor laser beams with the focuses of the first lens so that the laser beams are emitted in parallel at the required degree by the first lens, and at the same time making the optical axis of the parallel beams radiated from the first lens roughly parallel with the lens axis of the first lens (in other words, the radiation angle of the beam emitted from the first lens—the angle made by the beam axis of the emitted light and the axis of the first lens—is approximately zero). In addition when the laser emission point of the said semiconductor lasers cannot be properly adjusted with the focuses of the first lenses, and the optical axis of the parallel beams is slightly inclined towards the lens axis of the first lenses, these inclined parallel beams must be made to strike the second lens at right angles and in a specified position. Because these adjustments have to be made to within several microns precision, previously known semiconductor laser treatment devices required extremely sophisticated techniques, and have the disadvantage that the semiconductor laser treatment device is difficult to assemble initially, and all subsequent adjustments during maintenance, inspection, and replacement of the semiconductor lasers require the device to be returned to the manufacturer for specialist handling.

The second disadvantage of prior art is that during a power check of the laser beam, there must be enough space to place a separate power check unit alongside the semiconductor laser treatment device. Where no space is available, a separate table must be provided alongside the semiconductor laser treatment device, involving some inconvenience. This method has another disadvantage in that the results of meter reading will vary somewhat since the operator is required to make the final judgement on whether the semiconductor laser treatment unit is usable or not from the movement of the meter which converts the laser beam to an electric signal.

The third disadvantage is that because the laser radiation device is operated by hand to radiate beams using a power check photo-sensor, the operator radiating the laser beam estimates the central point of the photo-sensor by eye, leading to laser beams radiated diagonally to the photo-sensor or at different distances from the photo-sensor. This causes differences in the receiving of the laser beams and thus to variations in the measurements, giving rise to inconsistencies in the results of power checks.

Fourthly, to the applicant's knowledge, prior art using touch sensors indicate the operation of the touch sensor by simultaneously sounding a buzzer or displaying a lamp which shows "In use". Even when the touch sensor is simply in contact with the patient's skin and laser beams are not actually being emitted, both patients and operators may think that laser beams are being emitted, thus posing a problem during treatment.

The fifth problem with prior art is because the time display which indicates the laser beam emission time operates by counting backwards from a preset time to zero, where treatment extends past the initial preset time and the device is re-operated, there is no way of calculating the total emission time aside from noting the previous emission time on a piece of paper and adding it to the new time.

The sixth disadvantage of the prior art is that because the touch sensor is fixed, some patients feel an unpleasant sensation when it is pressed on the treatment area.

DISCLOSURE OF THE INVENTION

To solve the problems described above, this invention consisting of a laser radiation device and a control box housing a control mechanism which controls the laser radiation device via a cable, is provided with a cap which has a pair of touch sensors in the vicinity of the laser beam emission aperture; it also has inside it, multiple semiconductor lasers and lensess for forming a laser beam used for medical treatment by focusing to a single point the laser beams emitted in parallel from these multiple semiconductor lasers. The invention has the following benefits.

The first invention is characterized by having a series of first lenses, each corresponding to a semiconductor laser, designed for making the laser beams emitted from each of the semiconductor lasers parallel, and a second lens which collects these multiple parallel beams and focuses them to a single point to obtain a treatment laser beam. Each of these semiconductor lasers is supported in its own laser holder, these laser holders fitting closely into multiple insertion holes provided at specified places on the circumference of the body of the laser radiation device, and corresponding approximately to the position of incidence of the laser beams on the second lens. Each of these first lenses is held individually by a lens holder provided with a support hole having an inside diameter approximately equal to the outside diameter of the first lens, in a manner such that the position of the first lens can be adjusted forwards or backwards within these support hole; this lens holder is respectively mounted at the tip of the laser holder using a screw which passes through the screw hole constructed in the lens holder and screws into a female screw at the end of the laser holder. The said laser holder and a lens holder together form a subassembly which is attached by fitting the laser holder into the insertion holes in the body of the device. The position of the first lens can be adjusted both forwards and backwards in the support hole, and the position of the lens holder can be adjusted both horizontally and vertically in relation to the laser holder by using the narrow clearance provided between the screw and the screw hole. This permits the semiconductor laser and the first lens to be positioned at several tens or several microns precision at the circumferences in relation to the second lens, simply by fitting the laser holder tightly into the insertion holes, thus attaching it to the body. Secondly, various adjustments can be made in the subassembly before it is attached to the body of the device; these include the alignment of the semiconductor laser emission point and the focus of the first lenses, ie the parallelism of the laser beams from the first lens and the angle of emission of beams from the first lens to be adjusted by adjusting the mount position of the lens holder in relation to the laser holder by altering the forward/backward position at which the first lens is held in its support hole and the clearance between the screw and the screw hole. Thus the laser beams emitted from the the multiple semiconductor lasers can be made to converge at the required focal point for medical treatment. The replacement of the semiconductor lasers involves simply the replacement of a pre-adjusted subassembly body, and so can now be performed easily and quickly by anyone, without special skill being required.

The second invention is characterized by being provided with a series of first lenses, each corresponding to a semiconductor laser and used for making the laser beams emitted by the semiconductor lasers parallel, these multiple laser beams being focused to a single point by a second lens which collects the beams, thus making a laser beam for use in medical treatment; at the same time, each of the semiconductor lasers is held by individual laser holders, these laser holders fitted tightly into multiple insertion holes provided at specified places on the circumference which correspond to the positions at which the laser beams fall on the second lens. Further each of the first lenses is supported in a lens holder comprising a rotational body provided with a support hole with an internal diameter which is approximately equal to the external diameter of the first lens, and a base with a curved surface hole in which the rotational body is fixed so that it can rotates in all directions, making the lens self-adjustable forwards and backwards within the hole. The lens holder is mounted at the end of the laser holder by a screw which passes through a screw hole in its base and screws into a female screw hole at the end of the laser holder. The said laser holder and the lens holder form a subassembly which is fixed to the body when the laser holder is inserted in the insertion holes; in this subassembly the first lens can be adjusted in its support hole and mounted position of the lens holder can be adjusted horizontally and vertically in relation to the laser holder using the narrow clearance between the screw and the screw hole. Further, by rotating the rotational body in relation to the base, the beams emitted from the first lens can be made to fall at right angles to the second lens, and the angle of the lens axis of the first lens can be adjusted in relation to the lens axis of the second lens. As a result, slanted laser beams ie those beams for which the first lens was not sufficiently aligned with the semiconductor laser emission point so that the light beam axis is slightly inclined towards the lens axis, can be adjusted so that the laser beams fall at right angles to the second lens and at a specified position, simply by inclining the lens axis of the first lens which is supported by the rotational body by rotating it in relation to the base.

In the third invention, the said control mechanism is constructed of a first control mechanism and a second control mechanism. The first control mechanism is characterized by being provided with a radiation control circuit which controls the emission of the laser beams, a fixed current circuit which stabilizes the signals from the said radiation control circuit, semiconductor lasers which emit laser beams on a signal from the set current circuit, an addition circuit which adds the emission states of the said semiconductor lasers and a touch switch which goes on when touched against the human body; the second control mechanism is characterized by having an input processing circuit, a time display circuit, a power check circuit and a radiation laser beam check circuit; the input processing circuit being provided respectively with a first memory circuit which records the on/off status of the manual switch which starts the output of laser beams via the radiation control circuit, a second memory circuit which similarly records the on/off status of the stop switch which stops the laser beam output via the radiation control circuit, a first AND circuit which is connected to the first and second memory circuits and calculates the logical product of both the manual and stop switches, a second AND circuit which calculates the logical product of the first and second memory circuits and the touch switch circuit, and an OR circuit which calculates the logical sum of the first and second AND circuits; the time display circuit is provided with a radiation time display lamp which displays the accumulated laser beam emission time calculated by an addition formula using signals from the input processing circuit giving the on state of the manual switch and the on status of the touch switch; the time calculation circuit having a radiation time set circuit which records a preset time and a preset counter which adds the laser beam emission time until the preset time is reached, and halts the emission of laser beams when the laser beam emission time and the preset counter accumulated time are equal; the power check circuit is provided respectively with a photosensor which receives the laser beams from the semiconductor laser and converts the optical intensity of laser beams to an electric signal, a comparator which accepts the optical intensity converted to the said electric signal as a "received light value" and compares it against a preset standard value for laser beams; and a radiation laser beam check circuit which issues a warning of reduced laser beam output when the result of the comparison with the signal from the addition circuit is lower than the standard value. This thus permits the output intensity of laser beams emitted from the first control circuit to be checked by the second control circuit; by radiating a focused laser beam on the photo-sensor which is incorporated in the power check control circuit, the comparator can compare the output of the focused laser beams received by this photo-sensor with a preset standard value by the comparator, the result of the comparison being displayed selectively in the control box as a positive or a negative value, thus providing a fast, easy and accurate power check.

In the fourth invention a concave housing is formed in the control box, the housing used for a power check and also aproximately corresponding to the shape of the cap of the laser radiation device, and further characterized by being provided on the bottom surface of the concave housing with a photo-sensor for receiving laser beams, set in a position which, while the laser radiation device is housed, corresponds to the emission aperture, and is at right angles to the direction of laser beam emission. Thus because the concave housing is made to correspond approximately to the shape of the cap, the interior surfaces of the concave housing act as guides and the laser radiation device is inserted through its own weight (shown in lower part of FIG. 9) and cannot be inserted in an incorrect position; thus the laser radiation device (in particular the cap) is correctly positioned for storage in the housing regardless of who has been using it. In this position the laser beams are emitted onto the photosensor, thus enabling a check of whether sufficient power is available for treatment to be carried out simply and accurately.

In the fifth invention the laser radiation device is characterized by having a luminous body in the cap which lights up when it detects some laser beams emitted from the laser radiation device; the control box also is provided with a self-illiminating laser mark which displays laser beam emissions directly when they are detected from the semiconductor laser; it also has a time display which uses an addition formula to calculate the accumulated emission time. Thus, the cap itself appears to be luminous through the lighting up of the luminous body in the laser radiation device when some laser beams are detected during laser beam emission, permitting the operator to tell that laser beams are being emitted without releasing his eyes from the treatment area; other people in the vicinity can also tell that laser beams are being emitted because the laser mark on the control box lights up when laser beams are detected from the laser radiation device. Also since the time display gives a display of the accumulated laser beam emission time, the total radiation time can now be conveniently assessed at a glance even if the time has been reset because of insufficient initial treatment time.

Finally in the sixth invention the laser radiation device is characterized by being provided with touch sensors which are protrudable and retractable in relation to the treatment area. Therefore when pressed against the treatment area, the touch sensors retract into the cap and thus do not give the patient an unpleasant sensation.

PREFERRED EMBODIMENTS OF THE INVENTION

The section which follows describes, with reference to the attached drawings, a series of embodiments of this invention. The embodiments will be described as Embodiment A,B,C,D, where A is the first invention, B is the second invention, C is the third invention, and D corresponds to the fourth, fifth and sixth inventions respectively. In this description, the words "front" and "tip" indicate the direction of laser beam emission, while "back" indicates the opposite direction. Therefore, the arrow Z in FIG. 4 indicates a forwards/backwards direction, while the X and Y directions arrowed indicate left/right (horizontal) and up/down (vertical) directions. Further in the following descriptions of the embodiments, the common or similar parts have been given the same code, and any duplicate description has been omitted.

Embodiment A

Figures 1, 2, 3:
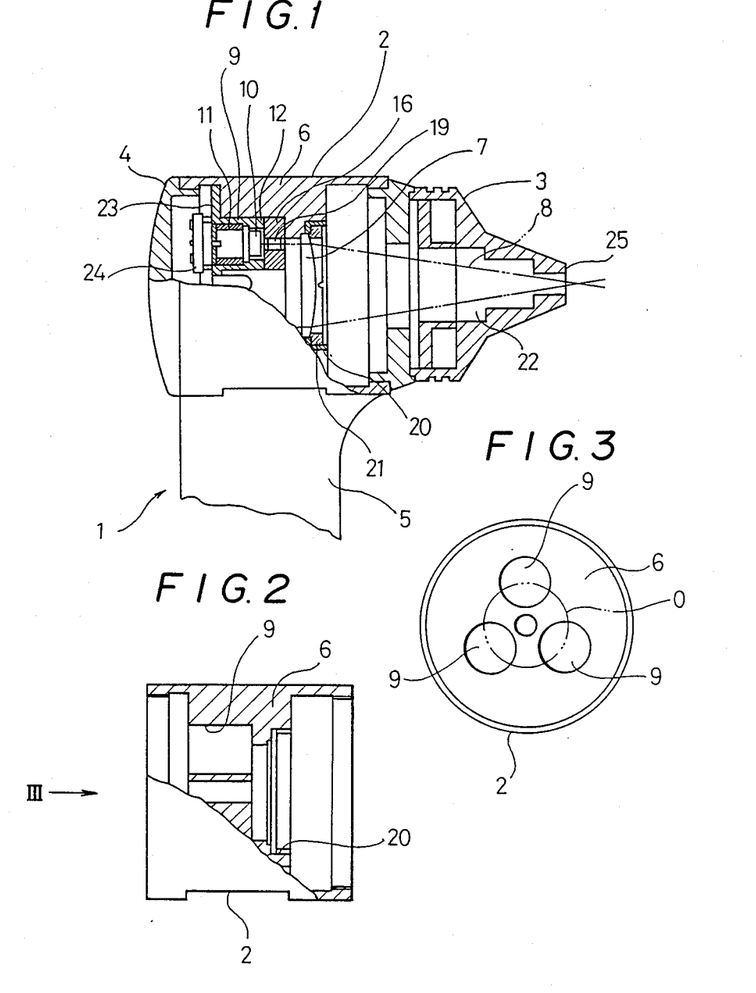
FIG. 1 is an outline side view including a partial cross-section of the laser radiation device.
FIG. 2 is an outline side view includes a partial cross-section of the body only.
FIG. 3 is an outline side view of the body viewed from the direction of the arrow III in FIG. 2.

The laser radiation device 1 of this semiconductor laser treatment unit is formed from an outer cover comprising a body 2, a cap 3 which is fixed to the front of this body 2, and a cover 4 which covers the back of the body 2; a clip 5 is attached to the bottom part of the body.

The inside of this cylindrical body 2 is provided with a flange 6, which has insertion holes 9 arrayed at three approximately equal intervals on the circumference 0 and accurately matching the position of incidence of the laser beam 8 on the second lens 7 (described below) on this flange 6. The cylindrical laser holder 12 into which the semiconductor laser 10 is internally fixed by a laser press-fit ring 11, fits closely into these three insertion holes 9. The tip of this laser holder 12 has a female screw hole 13, and the lens holder 16 is mounted using the screw 14 which screws into this female screw hole 13, through the screw hole 15 which has a narrow clearance in relation to screw 14. The lens holder 16 and the laser holder 12 make up a subassembly 17, with a cylindrical lens 19 being supported as the "first lens" in the support holes 18 of the lens holder 16. Further, the front of the flange 6 has a stepped part 20 with a flat convex lens 7 supported as the "second lens" on this stepped part 20 by a press-fit ring 21. This semiconductor laser treatment unit has therefore, a semiconductor laser 10, and two linearly arranged lenses, a cylindrical lens 19 as the "first lens" and a flat convex lens 7 as the "second lens".

The cap 3 has a coned external shape, with an internal passage 22 for laser beams 8.

The integrated circuits 24 for controlling the semiconductor lasers 10 are screwed into and held on the flange 23 at the end of the laser holder 12, using spacers not shown.

In relation to the emission and focusing of the laser beams 8 by the semiconductor laser treatment unit; the laser beams 8 emitted from the semiconductor lasers 10 are first made parallel by the cylindrical lens 19, and then are refracted and focussed by flat convex lens 7 so that they converge at a point a little past the tip 25 of the cap 3, thus forming a laser beam used in medical treatment.

Figure 4:
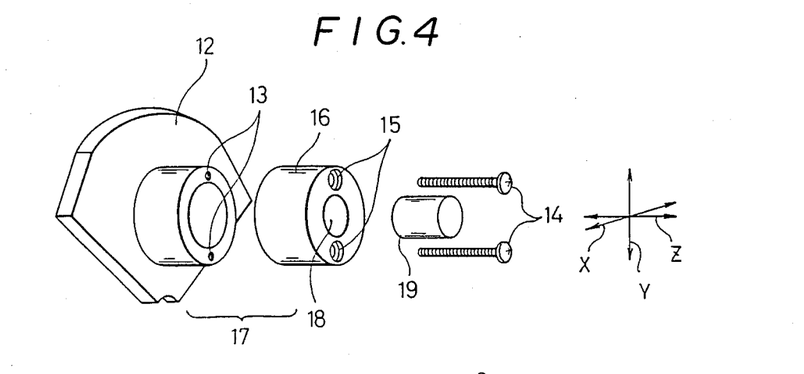
FIG. 4 is an outline perspective view of the overall relation between the laser holder, the lens holder, the screws and the cylindrical lenses used as "first lenses".
Figure 5:
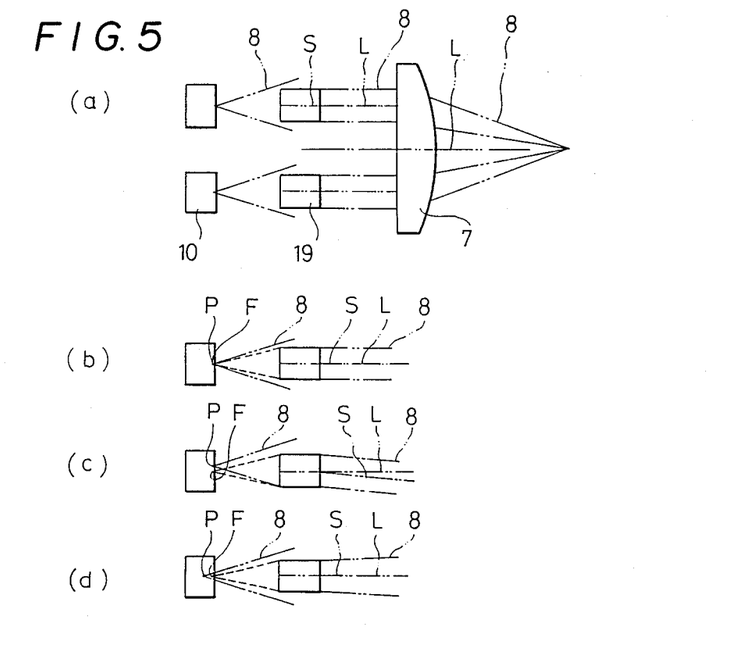
FIGS. 5(a) through 5(d) are descriptive drawing showing alignments of the semiconductor lasers, the cylindrical lenses and the second lens, the adjustment relationship between the semiconductor laser beam emission point and their convergence on the cylindrical lens, and the relationship between the laser beams.

The optical laser beams 8 can be focused in this semiconductor laser treatment unit as follows. First, before mounting the subassembly 17 on the body 2, the parallelism of the optical beams radiated from the cylindrical lens 19 can be adjusted by adjusting the position of the cylindrical lens 19 forwards or backwards in its holder hole, in the direction of the arrow Z, and adjusting the emission point P and the focus F of the cylindrical lens 19 in the direction of the arrow Z. Then the mounted position of the lens holder 12 in relation to the laser holder 16 can be adjusted by adjusting in the directions of the arrows X and Y, the clearance between the screws 14 used to mount the lens holder and the screw hole 15, and the adjusting the emission point P of the semiconductor laser 10 and the focus point F of the cylindrical lens 19, in the direction of the arrows X and Y, so that the radiation angle ie the angle formed between the optical axis S of the radiated beams and the lens axis L of the cylindrical lens 19, is approximately zero. Next by inserting the laser holder 12 in the emission aperture 9 provided precisely on the circumference 0, the adjusted subassembly 17 is attached to the body 2 and the semiconductor laser 10 and the cylindrical lens 19 can be positioned in relation to the flat convex lens 7 with between several tens and several microns accuracy.

In other words, this semiconductor laser treatment unit, firstly enables a semiconductor laser 10 and a cylindrical lens 19 to be positioned in relation to a flat convex lens 7 with an accuracy within the range of several tens of microns to several microns, by simply attaching subassembly 17 to body 2 by fitting laser holder 12 closely into insertion holes 9. Secondly, prior to mounting the subassembly 17 on the body 2, the emission point P of the semiconductor laser 10 and the focal point F of the cylindrical lens 19 can be aligned by adjusting the parallel emission of the optical beams 8 using the cylindrical lens 19, and also adjusting the angle of emission of the beams refracted from the cylindrical lens 19, by changing the forwards/backwards position of the cylindrical lens 19 in its support hole and adjusting the mounted position of the lens holder 16 on the laser holder 12 using the narrow clearance between screw 14 and the screw hole 15. This permits the laser beams 8 emitted from the multiple semiconductor lasers 10 to be easily focused to the required point of convergence to produce a laser beam for use in medical treatment. Replacement of the semiconductor lasers 10 involves a simple replacement of the subassembly, and can be easily and quickly carried out by anyone without special skills.

Embodiment B

Figure 6:
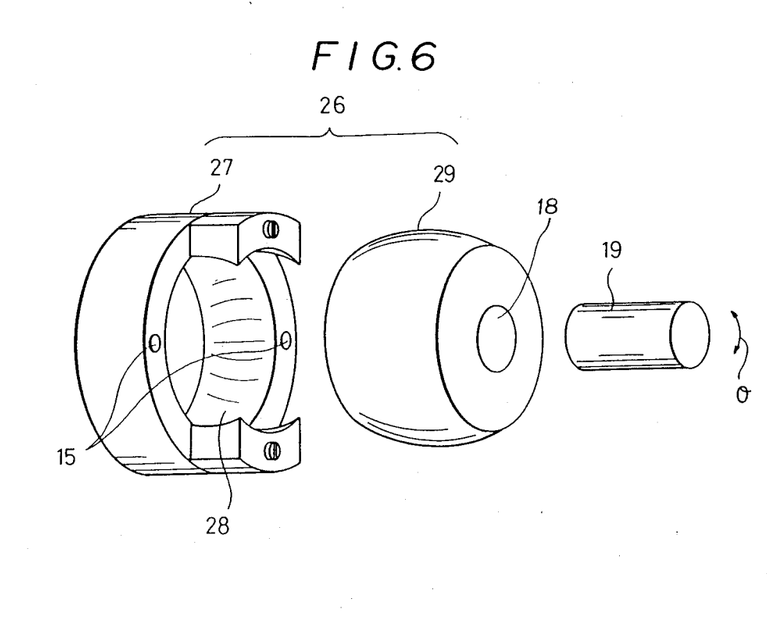
FIG. 6 is an outline perspective view showing the the lens holder assembly.

The lens holder 26 of the laser radiation device 1 in this semiconductor laser treatment unit is constructed of a base 27 having screw holes 15, and a rotational part 29 mounted so that it rotates freely in all directions, in a curved surface hole 28 provided in the base 27. The cylindrical lens 19 is supported in a support hole 18 in the same way as in Embodiment A described above, with the addition of the rotational part 29.

Therefore, in this semiconductor laser treatment unit, when the emission point P of the semiconductor laser 10 and the focal point F of the cylindrical lens 19 cannot be sufficiently aligned and because the optical axis S is leaning slightly towards the lens axis L, some adjustment is required to make the inclined optical beam fall at right angles and at a specified position on the flat convex lens 7; this adjustment is now easily performed by rotating the rotational part 29 in the direction of the arrow $\theta$ towards the base 27, and inclining the lens axis L of the cylindrical lens 19 which is supported in the lens support hole 18 in the rotational part 29 towards the lens axis L of the flat convex lens 7. This improves the convergence of the laser beams 8 in conjunction with the first and second actions described for the first invention above.

In the above explanation of the Embodiments A and B the adjustment of the cylindrical "first lens" 19 was described in relation to the directions X,Y,Z and $\theta$. It is of course possible that no adjustment is required at all, depending on the quality of the "semiconductor laser". The description above assumed that cylindrical lens 19 was to be used as the "first lens", but other types of lenses such as a "flat convex lens" or a "non-spherical lens" can also be used; in short, any lens which can be used to make a laser beam emitted from a semiconductor laser parallel is suitable. Therefore the above description could apply equally well to a "flat convex lens" or a "non-spherical lens".

Embodiment C

Figure 7:
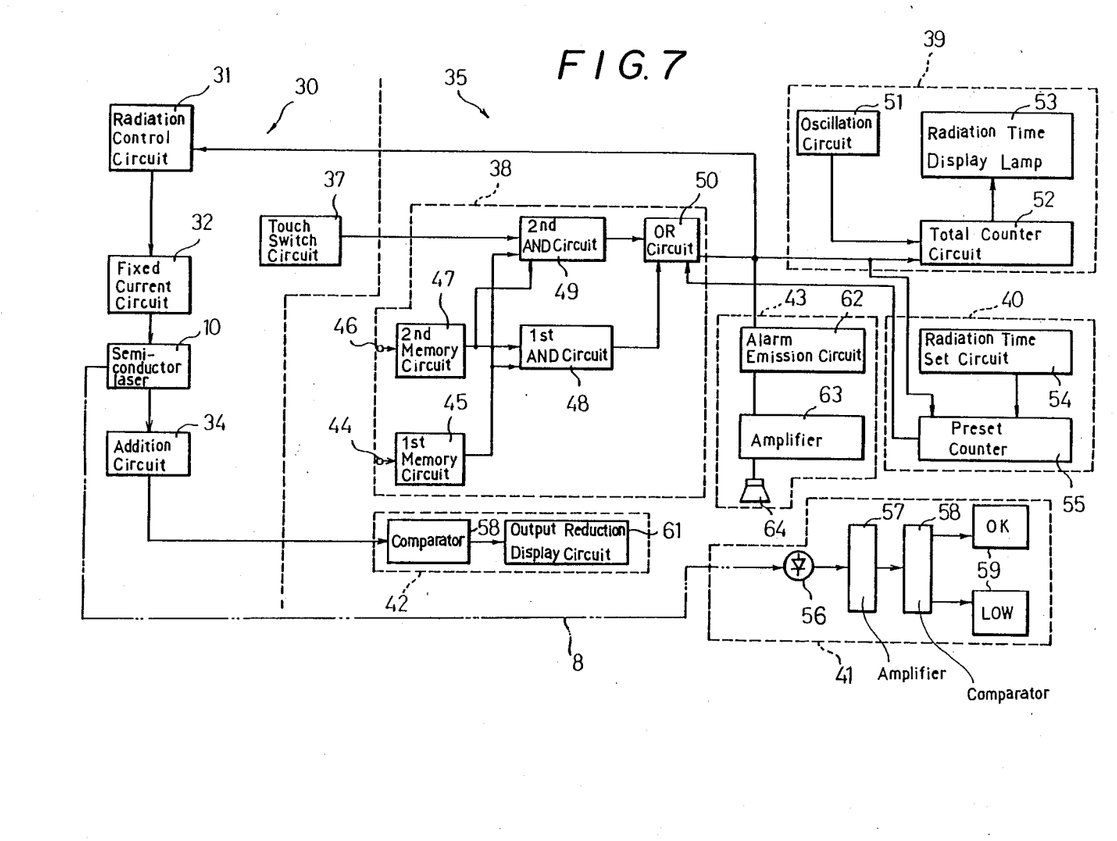
FIG. 7 is a circuit diagram showing the probe circuits incorporated in the control mechanism and the control circuits.

This semiconductor laser treatment unit has a control mechanism which is provided with a first control circuit 30 and a second control circuit 35.

The first control circuit 30 consists of a radiation control circuit 31, a fixed current control circuit 32, a semiconductor laser 10, an addition circuit 34 and a touch switch circuit 37. The radiation control circuit 31 is a circuit used to control the emission of laser beams 8 through operation signals from the second control circuit 35; it thus transmits a stable electric current to the semiconductor laser 10 via the fixed current circuit 32. The addition circuit 34 is a circuit which adds the electric signals of the "light beams" emitted from each of the semiconductor lasers 10. For example, when one of the semiconductors lasers 10 is not operating, the calculated electric signal is lower than the result obtained when all the semiconductor lasers are operating. In addition to the "radiation system" for the laser beams 8 comprising the fixed current circuit 32 and the semiconductor lasers 10, the first control circuit 30 is also provided with a separate touch switch circuit 37 not shown in the drawing, which switches ON when it touches the human body.

The second control circuit 35 is constructed of an input processing circuit 38, a time display circuit 39, a time calculation circuit 40, a power check circuit 41, a radiation laser beam check circuit 42 and an alarm circuit 43.

The input processing circuit 38 comprises primarily a manual switch 44, a first memory circuit 45, a stop switch 46, a second memory circuit 47, a first AND circuit 48, a second AND circuit 49 and an OR circuit 50. The first memory circuit 45 records the ON/OFF status of the manual switch 44 which starts the output of laser beams 8 from the said second control circuit; it is connected to the first AND circuit 49 and the second AND circuit 49. The second memory circuit 47 records the ON/OFF status of the stop switch 46 which stops the output of the laser beams 8; it is connected to the first and second AND circuits 48, 49 respectively. Further, the second AND circuit 49 is connected so that it receives signals from the touch switch circuit 37. The first AND circuit 48 calculates the logical product of an on state of the manual switch 44 and an off state of the stop switch 46; while the second AND circuit 49 calculates the logical product of an off state of the manual switch 44, an off state of the stop switch 46, and an on state of the touch switch circuit 37. The above states are transmitted to the OR circuit 50 as output from the first AND circuit 48 and the second AND circuit 49 respectively, and their logical sum is calculated. In the second AND circuit, if the manual switch 44 is on, the on/off state of the touch switch circuit 37 is disregarded. In other words, whatever its state, and only in this case, if the manual switch 44 is on, the stop switch 46 is off and the touch switch circuit 37 is on, or when the manual switch 44 is on and the stop switch 46 is off, a signal indicating emission of laser beams 8 from the input processing circuit 38 is transmitted to the said radiation control circuit 31 and others.

The time display control circuit 39 consists of an oscillation circuit 1, a total counter circuit 52 and a radiation time display lamp 53. This circuit uses a calculation formula in the total counter circuit 52 to accumulate time in units set by the oscillation circuit 51 only during radiation of laser beams 8 via signals from the said input processing circuit 38 to switch on the manual switch 44 or switch on the touch switch circuit 37. It then displays the total time using a radiation time display lamp 53. The total time accumulated by the said total counter circuit 52 ie the accumulated time of laser beam 8 emission, is initialized only when the total counter circuit 52 is reset.

The time calculation circuit 40 consists of a radiation time set circuit 54 which records a pre-set time for radiation with laser beams 8, and a pre-set counter 55 which calculates the radiation time for laser beams 8 until the set radiation time in the radiation time set counter 54 is reached. In this time calculation circuit 22, the radiation time calculated in pre-set counter 55 is compared with radiation set time, and radiation of laser beams 8 is stopped when the times match.

The power check circuit 41 comprises a "light receiving element" photo-element 56, an amplifier 57, a comparator 58 and a display part 59. The laser beam 8 radiated from the said semiconductor laser 10 is received by the photo-sensor 56 the strength of the laser beam 8 is assessed as its "intensity", converted to an electric signal as a "received light value", which is then amplified. In the comparator 58, the said "received light value" is compared with a "standard value", a value which indicates the minium volume of laser beams 8 necessary for treatment. The result of the comparison determines whether the unit can be used or not; if it can be used, "OK" is displayed in display part 59; if not, "LOW" is displayed in the connected display part 59, thus permitting the user to determine at a glance whether the semiconductor laser treatment unit is suitable for use or not.

The incorporation of the power check circuit 41 in the second control circuit 35 is an important feature of this invention.

The radiation laser beam check circuit 42 is connected to the said addition circuit 34 and comprises a comparator 58 which compares the signals from the addition circuit 34, and a reduced output display circuit 61. The comparator 58 contains a preset "standard value" for the amount of laser beam radiation necessary for treatment, and continually compares the electric signals which indicates the intensity of laser beams 8 in the those emissions transmitted via the addition circuit 34. When the result of the comparison is lower than the "standard value", ie the output of laser beams 8 being emitted has fallen, this fact is displayed by the output reduction display circuit 61, indicating that the volume of output laser beams 8 has been reduced to abnormally low levels. Lamps visible to the eye, or an audible buzzer may be used for this output reduction display circuit 61.

The alarm circuit 43 consists of an alarm generation circuit 62, an amplifier 63 and a speaker 64. When an error is detected in the laser beam 8 or in any of the aforementioned circuits, this abnormal signal is received and the alarm generation circuit 62 generates an abnormal signal such as lighting up a lamp and gives an alarm via the amplifier 63 through the speaker.

The following describes the use of the semiconductor laser treatment unit for a "power check".

When both the manual switch 44 and the stop switch 46 are on (the touch switch circuit 37 may be either on or off), a signal indicating that emission of laser beams 8 is possible is transmitted to the first control circuit 30 from the input processing circuit 38 via the second AND circuit 49 and the OR circuit 50. The first control circuit 30 causes laser beams 8 to be emitted from the semiconductor laser 10 through a signal transmitted from the radiation control circuit 31 to the fixed current circuit 32. When laser beams 8 are emitted to the power check circuit 41 incorporated in the second control circuit 35, the photo-sensor 56 receives the laser beam 8 and converts the intensity of the laser beam 8 to an electric signal and then performs a simple "power check" by comparing this received light value with a preset standard value for laser beams 8. Because the result of the power check, ie the result of the comparison of the received light value and a standard value for laser beams 8, is displayed as "OK" or "LOW" in the display part 59, it is easier to tell at a glance whether the unit is usable or not than with the previous method which used the oscillation of a meter (not shown).

Embodiment D

Figure 8:
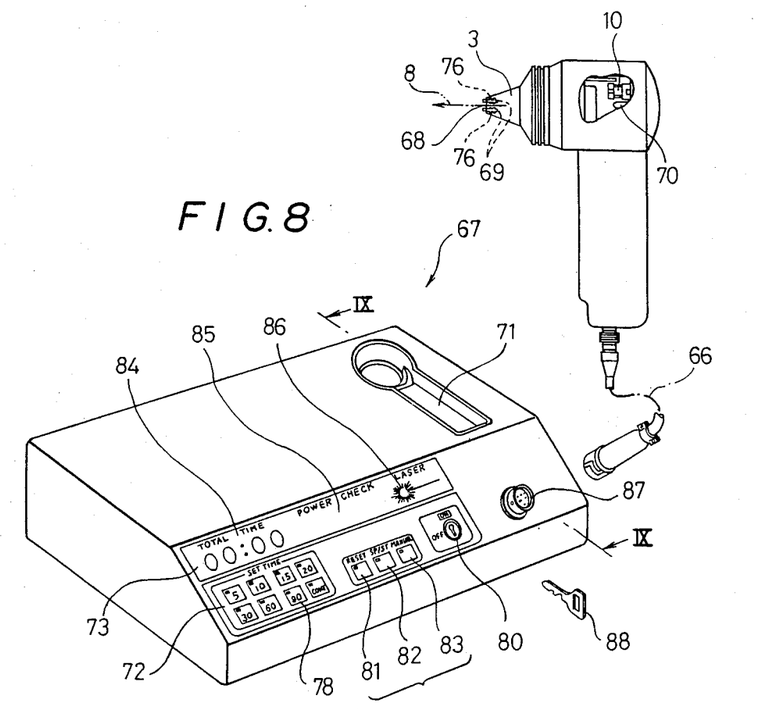
FIG. 8 is an overall perspective view of the semiconductor laser treatment unit.

This semiconductor laser treatment unit, is constructed primarily of a laser radiation device 1 and a control box 67 connected to the laser radiation device via a cable 66. An emission aperture 68 through which the laser beams 8 are radiated from the semiconductor laser 10 to the outside is provided in cap 3, and in the vicinity of the said emission aperture 68 are constructed touch sensors 69 for detecting the treatment area. The touch sensors 69 are a pair of pins which can detect that they are in contact with human body and separate their guides when pressed against the human skin (treatment area) (not shown), permitting the radiation of laser beams 8 through the guides. The touch sensors 69 are movable backwards and forwards using known means such as wings 76, and when they are pressed against treatment area and held there, the touch sensors 69 retract into the inside of the cap 3. This is also one of this invention's great benefits.

Further, a luminous body 70 is provided inside the laser radiation device 1, this luminous body 70 radiating by sensing part of the laser beam 8 from the semiconductor laser 10. This light hits the cap 3 and is dispersed, causing it to appear from the outside as if the cap 3 itself is luminescent. This is used as a clear sign of current "laser emission". Also because the luminous body 70 radiates light when it detects some laser beams 8 from semiconductor laser 10, it gives an indication of actual "laser emission". This is another of this invention's important features.

The control box 67 is constructed of a concave housing 71 used both for holding the laser radiation device 1 and for the power check, an operation panel 72 and a display panel part 73.

Figure 9:
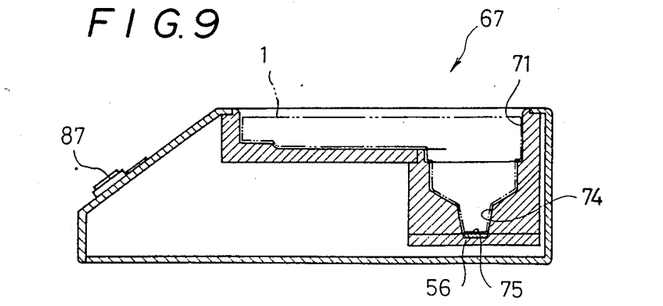
FIG. 9 is an overall cross-sectional view of the control box from the direction of the arrow line IX—IX in FIG. 8.

The concave housing 71 is constructed in the upper part of the control box 67 as shown in the cross section drawing FIG. 9, and is also designed for the power checks. It presents a shape which almost conforms to the one side of the cap 3 of the laser radiation device. In other words, a cap guide hole 74 is constructed in the housing in the shape of the tapering cap 3, and further a photo-sensor 56 for receiving laser beams is fixed on the bottom surface part 75 corresponding to the emission aperture 68, in a direction at right angles to the emission direction of laser beams 8. While the laser radiation device 1 is still housed in this concave housing 71 before being used for treatment, a power check can be performd to indicate whether or not the laser beams 8 have sufficient power for the treatment. In other words, when laser beams 8 are emitted from the laser radiation device 1 housed in the concave part 71, the laser beams 8 hit the photo-sensor 56 at the bottom 75 of the housing, are converted to an electric signal which is electrically checked against a preset value, and the result of the check (either high or low) is indicated by the display panel 73 as either "OK" or "LOW". During the power checks, by operating the switches on the operation panel 72, it is possible to switch over to use of the touch sensor function ie the function which permits the emission of laser beams 8 between the pair of touch sensors 69 which are touching the human body (treatment area).

The operation panel 72 is constructed of a set timer 78, operation buttons and a key switch 80. The set timer 78 can be used to set the emission time for laser beams 8 to a value between 5 and 90 seconds, or can be set to continuous use, ie no time set. The operation buttons comprises a reset button 81, a stop/start button 82 and a manual button 83. By pressing the reset button 81 twice in succession, the accumulated emission time of laser beams 8 is totally cleared by an accumulation circuit (not shown in the drawing), so that the accumulated emission time of laser beams 8 can be re-accumulated from zero.

The stop/start button 82 is a switch which is used in an emergency to stop the emission of laser beams 8 being emitted through the touch sensor function. When it is pressed the emission of laser beams 8 is stopped and a lamp (not shown) lights up. The manual button 83 is used to start the laser beam output check in the "power check". When the manual button 83 is pressed, both the said stop/start button 82 and the manual button 83 light up; if the stop/start button 82 is again pressed at that point, laser beams 8 are emitted and a "power check" is performed whether the touch sensor function is operating or not (at this point the stop/start button will go off). Then if the stop/start button 82 is pressed again, the emission of laser beams 8 is stopped and the stop/start button 82 lights ups. The key switch 80 is the power connection/disconnection switch for the entire semiconductor laser treatment unit.

The display panel 70 is constructed of a time display 84, a power check display 85 and a laser mark 86. The time display 84 shows an accumulated display of the accumulated laser beam emission time, calculated using an addition formula up to a maximum number of 99 minutes 59 seconds. The provision of a time display 85 which can display the accumulated time calculated using an addition formula is one of the features of this invention. The power check display 85 displays the characters "OK" or "LOW" as a result of the said power check. The laser mark 86 lights up while the laser beams 8 are being emitted, and is used as one of the methods of "warning" the operator and the surrounding people that laser beams are being emitted; the ability of this invention to detect the laser beams 8 emitted from the semiconductor laser 10 and to display laser beam emission directly is one of its important features. If a problem occurs during emission of laser beams 8, the characters "CHECK" start blinking in the said power check display 85, indicating to the operator that a "power check" is required. 87 is a receptacle for connection of the cable 66 and 88 is a key.

The following describes the usage of the semiconductor laser treatment unit.

Power check:

When the laser radiation device 1 is housed in the concave housing 71, it can be positioned to the central part of the photo-sensor 56, without slanting the device, by moving it downwards (bottom part of FIG. 9) with the tapered cap 3 following the cap guide hole 74. This photo-sensor 56 is set at the bottom of the concave housing 71 at right angles to the direction of emission of the laser beams 8. Therefore, regardless of who has been handling the laser radiation device, it will be stored with the emission hole 68 pressed by its own weight and at right angles against the photo-sensor 56. So when the manual button 83 and the stop/start button 82 are pressed, the laser beams 8 are emitted from the emission aperture 68 onto the photo-sensor 56, permitting a "power check" of whether sufficient power can be output for treatment. Thus, compared to previous methods of checking power by applying laser beams to a hand-held power check photo-sensor 56, with problems such as the emission aperture 68 being diagonally positioned, or at different distances, in relation to the photo-sensor 56, it is now possible to carry out an accurate and consistent power check. Also, because the result of the "power check" is displayed in characters "OK" or "LOW" on the power check display 85, the usability of the device can be assessed at a glance.

Radiation of the treatment area by laser beams:

The laser radiation device 1 is taken out of the concave housing 71 and placed against the treatment area (not shown). At this point the projectable/retractable touch sensors 69 are retracted into the interior of the cap 3, but the touch sensor function ie the function which permits the emission of laser beams 8 through the pair of touch sensors 69 which are touching the patient's skin, still operates, laser beams 8 can still be emitted without the touch sensors 69 protruding through the front of the cap 3 to cause any unpleasant sensation to the patient.

Further, because the luminous body 70 within the laser radiation device 1, and the laser mark 86 in the control box 67, immediately light up when they detect some laser beams 8 from the semiconductor laser 10, there is an actual indication of "laser emission", through a technique which is much safer than that used in previous art in which the touch sensor function posted a warning using a lamp or a buzzer. Further, because the cap 3 itself shines through the action of the luminous body 70, without removing his eyes from the treatment area being treated to look at the laser mark 86, the operator can identify the emission of laser beams through the lighted cap, thus improving concentration and safety during operation.

Also since the accumulated emission time is calculated by counting the duration of emission of laser beams 8 using an addition formula and is displayed in the time display 84, the accumulated emission time can be seen at a glance even when the time has been reset because of insufficient emission for treatment. This feature makes operation more convenient.

Use in Industry

This series of inventions has a number of significant benefits as described above. The semiconductor laser treatment unit of the first invention permits the semiconductor laser and the first lens to be positioned on its circumference in alignment with the second lens to an accuracy of several tens to several microns; with the semiconductor laser and the first lenses so positioned, it permits the semiconductor laser emission point and the focus of the first lenses to be easily aligned, ie the parallel angles of the laser beams issued from the first lenses, and the angle of emission of the beams from the first lenses to be adjusted; and the laser beams emitted from the multiple semiconductor lasers to be focused to the degree of convergence required for medical treatment. Further, because the semiconductor lasers are replaced by replacing an entire pre-adjusted subassembly, this replacement can be performed by anyone and no special skills are required.

In the semiconductor laser treatment unit of the second invention, in addition to the benefits described above, even when the semiconductor laser emission point and the focal point of the first lens cannot be sufficiently adjusted, and the optical axis is slightly inclined towards the lens axis, the inclined beam can be easily made to hit the second lens at right angles and at a specified position. In conjunction with the above benefits, this results in even better focusing of the laser beams.

In the semiconductor laser treatment unit of the third invention, the incorporation of a power check circuit in the control circuit permits a power check to be carried out simply before the start of treatment, thus avoiding the inconvenience of having a power check unit which is separate from the semiconductor laser treatment unit. Also, the usability of the semiconductor laser treatment unit is displayed on a display, and can be assessed at a glance.

The semiconductor laser treatment unit of the fourth invention provides for the laser radiation device a concave housing with a shape which corresponds to the shape of the cap of the laser radiation device, thus permitting the device to be stored in an appropriate position. At the bottom of the concave housing there is a photo-sensor positioned at right-angles to the direction of laser beam emission; this means that regardless of who has been using it, the laser radiation device is always pressed into the housing at right angles and by its own weight, and cannot be placed on a slant or in the wrong position (distance) in relation to the photo-sensor. The receiving of laser beams by the photo-sensor is therefore uniform and thus enables an accurate and reproducible power check to be carried out. Also because the laser radiation device is housed in a concave housing, it is protected from damage and can be managed as one unit in its control box.

In the semiconductor laser treatment unit of the fifth invention, because the cap of the semiconductor laser itself becomes luminous through the action of the luminous body which emits light when some laser beams being emitted from the semiconductor laser are detected, it is possible to recognize the emission of laser beams without removing one's eyes from the treatment area to look at the control box. In addition to the operator, surrounding people can also recognize that laser beams are being emitted because a lamp on the control box lights up. Therefore because people in the vicinity of the device (the operator and others) are immediately warned that laser beams are being emitted, the safety of the device during actual laser beam emission is improved. Further, because the accumulated emission time can be determined at a glance from the display of a running count of the laser beam emission time, the total emission time can be determined easily even if the emission time is reset because of insufficient treatment time.

In the semiconductor laser treatment unit of the sixth invention, the touch sensors retract into the cap, thus avoiding any unpleasant sensation to the patient even if the device is pressed against the treatment area.

We claim:

1. In a semiconductor laser treatment unit comprising a laser radiation device and a control box which houses a control mechanism controlling the laser radiation device via a cable, the said laser radiation device including a body provided at a tip thereof with a cap having a pair of touch sensors in the vicinity of the emission aperture, and further being provided internally with multiple semiconductor lasers and a series of lenses which are used for making the laser beams emitted from the multiple semiconductor lasers parallel, and making them converge to a single point to form a laser beam for medical treatment, the said semiconductor laser treatment unit being characterized by the fact that each of the said lenses is constructed to correspond respectively with the said semiconductor lasers, with multiple first lenses used to make the laser beams issued from the multiple semiconductor lasers parallel, and a second lens which focuses these multiple parallel laser beams to a single point to form a laser beam used for treatment; each of the said semiconductor lasers being held in a laser holder, these laser holders being previously fitted tightly into insertion holes at a specified circumference on the body, the circumference approximately corresponding to the position of incidence of the laser beam on the second lens; each of the said first lenses being held individually in a lens holder provided with support holes with an internal diameter approximately equal to the external diameter of these first lenses, these lens holders having a screw hole and being individually mounted to the ends of the laser holders by being screwed to the ends of these laser holders by a female screw which passes through the screw hole, each of these said laser holders and lens holders forming a subassembly which is attached to the body by the fitting of the laser holder into its insertion hole; the position of the first lens being adjustable both forwards/backwards in its support holes and the position of lens holder being adjustable both vertically and horizontally in relation to the laser holder using the clearance constructed between the screw and the screw hole.

2. In a semiconductor laser treatment unit comprising a laser radiation device and a control box which houses a control mechanism controlling the laser radiation device via a cable, the said laser radiation device including a body provided at a tip thereof with a cap having a pair of touch sensors in the vicinity of the emission aperture, and further being provided internally with multiple semiconductor lasers and a series of lenses which are used for making the laser beams emitted from the multiple semiconductor lasers parallel, and making them converge to a single point to form a laser beam for medical treatment, the said semiconductor laser treatment unit being characterized by having multiple lenses corresponding to multiple semiconductor lasers, with multiple first lenses which make the laser beams emitted from these multiple semiconductor lasers parallel, and a second lens which focuses these multiple parallel beams to a single point, forming a laser beam for medical treatment; each of the said semiconductor lasers being held in a laser holder, these laser holders being previously fitted tightly into insertion holes at a specified circumference on the body of the said radiation device, the circumference approximately corresponding to the position of incidence of the laser beam on the second lens; each of the said first lenses being held individually in a lens holder which is constructed from a rotational body provided with support holes at an internal diameter approximately equal to the external diameter of the first lenses and a base which has curved holes into which are inserted the rotational body so that it can rotate in all directions, these lens holders having a screw hole in the base, so that they can be mounted at the end of the laser holder by the screwing of a screw through this screw hole into a female screw hole constructed in the end of the laser holder; each of these said laser holders and lens holders forming a subassembly which is attached to the body by the fitting of the laser holder into its insertion hole; in this subassembly, the position of the first lens being adjustable both forwards/backwards in its support holes and the position of the lens holder being adjustable both vertically and horizontally in relation to the laser holder using the clearance constructed between the screw and the screw hole, and further by rotating the rotational body against the base, the angle of the axis of the first lens can be adjusted in relation to the lens axis of the second lens on which the beams emitted from the first lens should fall approximately at right angles.

3. In a semiconductor laser treatment unit comprising a laser radiation device and a control box which houses a control mechanism controlling the laser radiation device via a cable, the said laser radiation device being provided at its tip with a cap having a pair of touch sensors in the vicinity of the emission aperture, and further being provided internally with multiple semiconductor lasers and a series of lenses which are used for making the laser beams emitted from the multiple semiconductor lasers parallel, and making them converge to a single point to form a laser beam for medical treatment, the said semiconductor laser treatment unit being characterized by having a control mechanism constructed of a first control mechanism and a second control mechanism, the first control mechanism comprising a radiation control circuit which controls the emission of laser beams, a fixed current control circuit which stabilizes the signals from the said radiation control circuit, a semiconductor laser which emits laser beams in response to a signal from the set current circuit, an addition circuit which calculates the emission status of the said semiconductor laser, and a touch sensor circuit which changes to an on state when it touches the human body; the second control circuit being constructed of an input processing circuit, a time display circuit, a time calculation circuit, a power check circuit and a emitted laser beam output check circuit; the input processing circuit comprising respectively a first memory circuit which records the on/off status of the manual switch which starts the output of laser beams via the radiation control circuit, a similar second control circuit which records the on/off status of the stop switch which stops the output of laser beams via the radiation control circuit, a first AND circuit which is connected to the first and second memory circuits and calculates the logical product of both the stop and the manual switches, a second AND circuit which calculates the logical product of both the first and second memory circuits and the touch switch circuit, and an OR circuit which calculates the logical sum of the first and second AND circuits; the time display circuit having a radiation time display lamp which displays the total laser beam emission time accumulated by an addition expression from the signals emitted by the input processing circuit when the manual switch is on or the touch switch circuit is on; the time calculation circuit being provided with a radiation time set circuit which records a pre set time, and a preset counter which adds the laser beam emission time until the preset time is reached, and has a function which halts the emission of laser beams when the laser beam emission time matches the time calculated by the preset counter; the power check circuit being provided with a photosensor which receives the laser beam from the semiconductor laser and converts the volume of laser beams to an electric signal, a comparator which accepts the beam volume just converted to the said electric signal as a received light value and compares it with a preset standard value for laser beams, and displays the result of the comparison which indicates whether the device is usable or not; the radiation laser beam check circuit being provided with a function which compares the signal from the addition circuit and warns of a reduction in laser beam output if the result of the comparison is lower than the standard value; and permitting the volume of laser beam output emitted from the first control circuit to be checked using the second control circuit.

4. In a semiconductor laser treatment unit comprising a laser radiation device and a control box which houses a control mechanism controlling the laser radiation device via a cable, the said laser radiation device being provided at its tip with a cap having a pair of touch sensors in the vicinity of the emission aperture, and further being provided internally with multiple semiconductor lasers and a series of lenses which are used for making the laser beams emitted from the multiple semiconductor lasers parallel, and making them converge to a single point to form a laser beam for medical treatment, the said semiconductor laser treatment unit being characterized by the said control box comprising a concave housing which corresponds approximately to the shape of the cap of the laser radiation device and is used for power checks, this concave housing having on its bottom surface a photosensor for detecting laser beams which when the laser radiation device is housed in the concave housing corresponds in position to its emission aperture, and is positioned at right angles to the direction of laser beam emission.

5. In a semiconductor laser treatment unit comprising a laser radiation device and a control box which houses a control mechanism controlling the laser radiation device via a cable, the said laser radiation device being provided at its tip with a cap having a pair of touch sensors in the vicinity of the emission aperture, and further being provided internally with multiple semiconductor lasers and a series of lenses which are used for making the laser beams emitted from the multiple semiconductor lasers parallel, and making them converge to a single point to form a laser beam for medical treatment, the said semiconductor laser treatment unit being characterized by having a luminous body which illuminates the cap of the said laser radiation device when it detects some laser beams from the semiconductor lasers, and further by having a control box which has a self-illuminating laser mark which directly displays the emission of laser beams when laser beams are detected from each of the semiconductor lasers, and also has a time display which displays the cumulative laser emission time calculated using an addition formula.

6. In a semiconductor laser treatment unit comprising a laser radiation device and a control box which houses a control mechanism controlling the laser radiation device via a cable, the same laser radiation device being provided at its tip with a cap having a pair of touch sensors in the vicinity of the emission aperture, and further being provided internally with multiple semiconductor lasers and a series of lenses which aree used for making the laser beams emitted from the multiple semiconductor lasers parallel, and making them converge to a single point to form a laser beam for medical treatment, the said semiconductor laser treatment unit being characterized by said touch sensors being projectable and retractable in relation to the treatment area to control the emission of said laser beam from said laser radiation device.

7. A laser radiation device in a semiconductor laser treatment unit, said laser radiation device comprising:

(a) a body including a plurality of insertion holes arranged around a specified circumference on the body;

(b) a plurality of semiconductor lasers mounted in said body, each semiconductor laser producing a laser beams;

(c) lens means mounted in said body for rendering said laser beams emitted from said semiconductor lasers parallel to each other and for then converging said parallel laser beams to a single point, said lens means including:

(i) a plurality of first lenses, each corresponding to a respective semiconductor laser and each said first lens rendering the laser beam emitted from the respective semiconductor laser parallel to laser beams emitted from the remaining semiconductor lasers, and (ii) a second lens which focuses the plurality of parallel laser beams to a single point;

(d) a plurality of subassembly means for holding and accurately aligning said lens means and said semiconductor lasers in said body, each said subassembly means having an outer shape and dimensions such that said subassembly means detachably fits in a tight manner within a respective insertion hole in said body along said specified circumference, said circumference corresponding approximately to the position of incidence of said laser beams on the second lens, each said subassembly means including:

(i) a plurality of laser holder means for holding said semiconductor lasers, each said laser holder means holding respective one of said semiconductor lasers; and (ii) a plurality of lens holding means for holding said plurality of first lenses, each said lens holding means being movable relative to a respective one of said laser holder means and each said lens holding means holding a respective first lens so as to permit relative movement between each lens holding means and the respective first lens such that movement of said lens holding means relative to the respective one of said laser holder means provides adjustment of the emission point of the respective semiconductor laser and such that movement of said first lens relative to said lens holding means provides adjustment of parallelism of optical beams radiated from the first lenses.

* * * * *

UNITED STATES PATENT AND TRADEMARK OFFICE
CERTIFICATE OF CORRECTION

PATENT NO. : 4,905,690

DATED : March 6, 1990

INVENTOR(S) : Toshio Ohshiro, et al

It is certified that error appears in the above-identified patent and that said Letters Patent is hereby corrected as shown below:

In claim 7, column 18, line 6, of the patent, change "beams" to --beam--.

Signed and Sealed this

Seventh Day of May, 1991

*Attest:*

HARRY F. MANBECK, JR.

*Attesting Officer*

*Commissioner of Patents and Trademarks*